United States Patent [19]
Strickler et al.

[11] Patent Number: 5,164,164
[45] Date of Patent: Nov. 17, 1992

[54] SELF ACTUATING SOLE WETTING APPARATUS

[76] Inventors: Robert W. Strickler, 845 Clearview Dr., San Jose, Calif. 95133; Marlin E. Presser, 21789 E. Highway 4, Stockton, Calif. 95215

[21] Appl. No.: 689,319

[22] Filed: Apr. 22, 1991

[51] Int. Cl.⁵ .................... A61L 2/00; B08B 1/00
[52] U.S. Cl. .................... 422/292; 422/300; 15/104.92
[58] Field of Search .................... 422/292, 297, 300; 15/104.92

[56] References Cited

U.S. PATENT DOCUMENTS

| | | | |
|---|---|---|---|
| 2,282,672 | 5/1942 | Nelson | 15/104.92 |
| 2,602,724 | 7/1952 | Batchelor | 15/104.92 |
| 2,604,377 | 7/1952 | Eames | 15/104.92 |
| 3,696,459 | 10/1972 | Kucera et al. | 15/104.92 |
| 4,425,677 | 1/1984 | Cox | 15/104.92 |
| 4,866,805 | 9/1989 | Oden et al. | 15/104.92 |
| 5,071,628 | 12/1991 | Alazat | 422/292 |

FOREIGN PATENT DOCUMENTS 2631532 11/1989 France .................... 15/104.92

Primary Examiner—Robert J. Warden
Assistant Examiner—T. A. Trembley
Attorney, Agent, or Firm—Michael J. Hughes

[57] ABSTRACT

A self actuating sole wetting device (10) is provided for use in treating the soles of shoes, feet, paws and the like with a wetting solution (20) selected for a particular hygienic purpose. The device (10) includes a sole receiving subassembly (14) and a peripheral structure subassembly (16) forming a tray, and a reservoir subassembly (18) for delivering the solution to the tray. Absorbent pad members (58, 60) allow wetting uneven surfaces and prevent splashing. Flow control on the reservoir prevents excessive depth and splashing. The sole wetting device is particularly adapted for use with animals such as dogs or in canine environments, to prevent the spread of parvo and other diseases.

12 Claims, 2 Drawing Sheets

SELF ACTUATING SOLE WETTING APPARATUS

TECHNICAL FIELD

The present invention relates generally to hygienic devices and more particularly to devices for preventing the transfer of contagious bacterial and viral infections which may be carried on the soles of feet, shoes or paws. The preferred embodiment of the present invention is a self actuating sole wetting apparatus for allowing a person or animal to step into a tray including cushioned inserts which result in the sole of the foot, paw or shoe being coated with a disinfectant solution.

DESCRIPTION OF THE PRIOR ART

Many diseases and maladies are carried by bacteria and viruses. These disease transmitting moieties, and the larger creatures which carry or propel them from place to place, are referred to as vectors.

One of the methods by which vectors are transmitted from one infected creature from another is by carrying on the soles of feet or on footwear. In this manner a vector which is able to survive on the floor or on the ground may be picked up on footwear or feet and carried to a new location. At this point the vector may create a new infection by entering a creature in a variety of ways.

One of the types of infection which has become a significant problem in the canine field in recent years is a vector known as parvovirus or, more simply, "parvo". Parvo is a particularly insidious malady which gives rise to a number of debilitating symptoms and is, to present knowledge, essentially incurable. The progress of Parvo may be arrested if treated in the very early stages, but even in such cases, recovery is usually not complete.

One of the characteristics of Parvo is that it is capable of remaining viable in damp earth, wet floors, feces or the like for a very long period of time. An epidemic may be started by an animal stepping in an area where the parvoviral vectors are present and then allowing the vector to enter the body either through an open sore or cut or, as is common in the case of canines, by licking the paws. Once one animal in a group has become infected it is likely that other animals within the group or area will also become infected. Especially since the Parvo condition is often dormant for an extended period of time, it is difficult to be certain which animals are infected and which are not.

A related viral disease, which is similar to and transmitted in the same manner as Parvo, is Cororavirus. Both viral diseases causes severe vomiting, diarrhea and dehydration in dogs. These diseases are especially dangerous to puppies.

Humans also act as vectors by carrying the virus from one area to another. For example, a human walking in the kennel of a disease area may pick up the virus on the sole of the shoes and carry it to a new location where it may infect additional animals. This possibility has been known for several years and various steps have been taken by individuals attempting to prevent the spread of Parvo.

The most common currently used method is to utilize a spray bottle filled with a disinfectant solution specifically selected for defeating the Parvo and Corora viruses. In this prior art method the person balances on one foot while spraying the sole of the other shoe. The position of the feet is then reversed and the other sole is sprayed. This method has several disadvantages including the potential danger of the balancing required, erratic wetting of the sole by an incomplete spray pattern, the spread of the spray causing wetting of areas that need not be treated, such as stockings and other clothing, and that an excess amount of the wetting solution is utilized due to the inefficiency of the method.

Another commonly utilized method of protecting against sole-carried vectors involves utilizing a shallow pan filled with a wetting solution. In this instance the person steps into the pan, thus insuring that the bottoms of the feet are thoroughly wetted, provided that the depth of the wetting solution within the pan is sufficient. Disadvantages of this method are that it is difficult to maintain a proper depth of wetting solution to sufficiently coat the soles without being so deep as to cause other problems, such as splashing, spillage, and tempting animals to drink therefrom. In addition, the typical pan may be slippery both inside and out. That is, the person may slip inside the pan or the pan may slide on the floor, either of which can result in potentially hazardous situations. It is especially important to avoid puddles forming on floors, since the typical wetting solution can rapidly discolor or deteriorate flooring materials when present in quantity. However, the small amount that is actually present on the soles of the shoes or feet is not usually a problem.

The disadvantages inherent in the above methods are especially applicable when the treatment is to be applied to an animal. Many animals are extremely reluctant to step into an actual liquid. Furthermore, many are reluctant to hold still while the bottoms of the paws are being sprayed. Therefore, it is desirable to utilize a method for wetting the soles of feet, paws or shoes which addresses and solves many of the above problems.

BRIEF DESCRIPTION OF THE INVENTION

It is therefore an object of the present invention to provide an apparatus which will adequately apply a disinfectant wetting solution to the soles of feet, paws or shoes without wetting any additional element.

It is another object of the present invention to provide a sole wetting device which is stable both interiorally and exteriorally.

It is another object of the present invention to provide a sole wetting device in which the level of liquid is maintained at the proper height in order to achieve proper wetting without allowing exposure of free liquid.

It is a further object of the present invention to provide a sole wetting device which requires a minimum of maintenance.

It is yet another object of the present invention to provide a sole wetting device which is not esthetically unattractive.

The present invention is a self actuating sole wetting apparatus particularly adapted for use by humans and animals to prevent the transmittal or carrying of disease vectors, viruses and the like, which may be carried on the soles of the feet. The preferred embodiment is a device which is especially directed at the problem of preventing the transfer of parvovirus, but is equally adaptable to a wide variety of other vector conditions. The device is intended for use with a liquid wetting solution including a disinfectant active chemical agent.

Briefly, a preferred embodiment of the present invention is a self actuating sole wetting apparatus in the nature of a specially formed tray including a plurality of compartments. Two of the compartments are designated as foot receiving compartments adapted to enclose compressible absorbent transfer pads upon which the user may step. The foot receiving compartments are separated by separation protrusions having fluid flow channels formed therebetween. A third major compartment is adapted for receiving a fluid container and to permit controlled dispensation of an antiseptic solution into fluid flow channels and to the absorbent pads. The preferred embodiment is primarily in the form of a single molded tray element with the removable components including the disinfectant container, a container cover and the absorbent pads. The tray member includes reinforcement ridges for strength purposes and mounting detents to enable the device to be secured to a floor or other flat horizontal surface.

An advantage of the present invention is that it is easily recognizable as to the purpose and utilized without undue thought or effort.

Another advantage of the present invention is that it results in thorough wetting of the ground-touching portion of the feet or shoes without wetting any additional portions.

A further advantage of the present invention is that it includes very little accessible liquid which might tempt an animal to drink therefrom.

Still another advantage of the present invention is that it prevents splashing and spilling.

A still further advantage of the present invention is that it is self actuating in keeping the level of liquid at the right amount to wet the absorbent pad and thus requires negligible maintenance.

A still further advantage of the present invention is that it does not include standing liquid and is thus readily usable with animals, which frequently have an aversion to stepping in liquids.

Still another advantage is that the invention may be utilized by simply standing in or carefully walking through the tray without requiring any special balancing or manipulation.

These and other objects and advantages of the present invention will become clear to those skilled in the art in view of the description best presently known mode of carrying out the invention and the industrial applicability of the preferred embodiment as described herein and as illustrated in the several FIGURES of the drawings.

BEST MODE OF CARRYING OUT THE INVENTION

The present invention is a self actuating sole wetting apparatus especially adapted for use in combating infectious vectors which maybe carried on the feet or the soles of footwear. The preferred embodiment of the device, although adapted to a wide variety of uses, is specifically intended for use in kennels and homes where the parvovirus threat is considered a significant factor. The invention is adapt to be utilized with a fluid wetting solution including a selected chemical agent adapted for attacking the particular vector involved.

Figure 1:
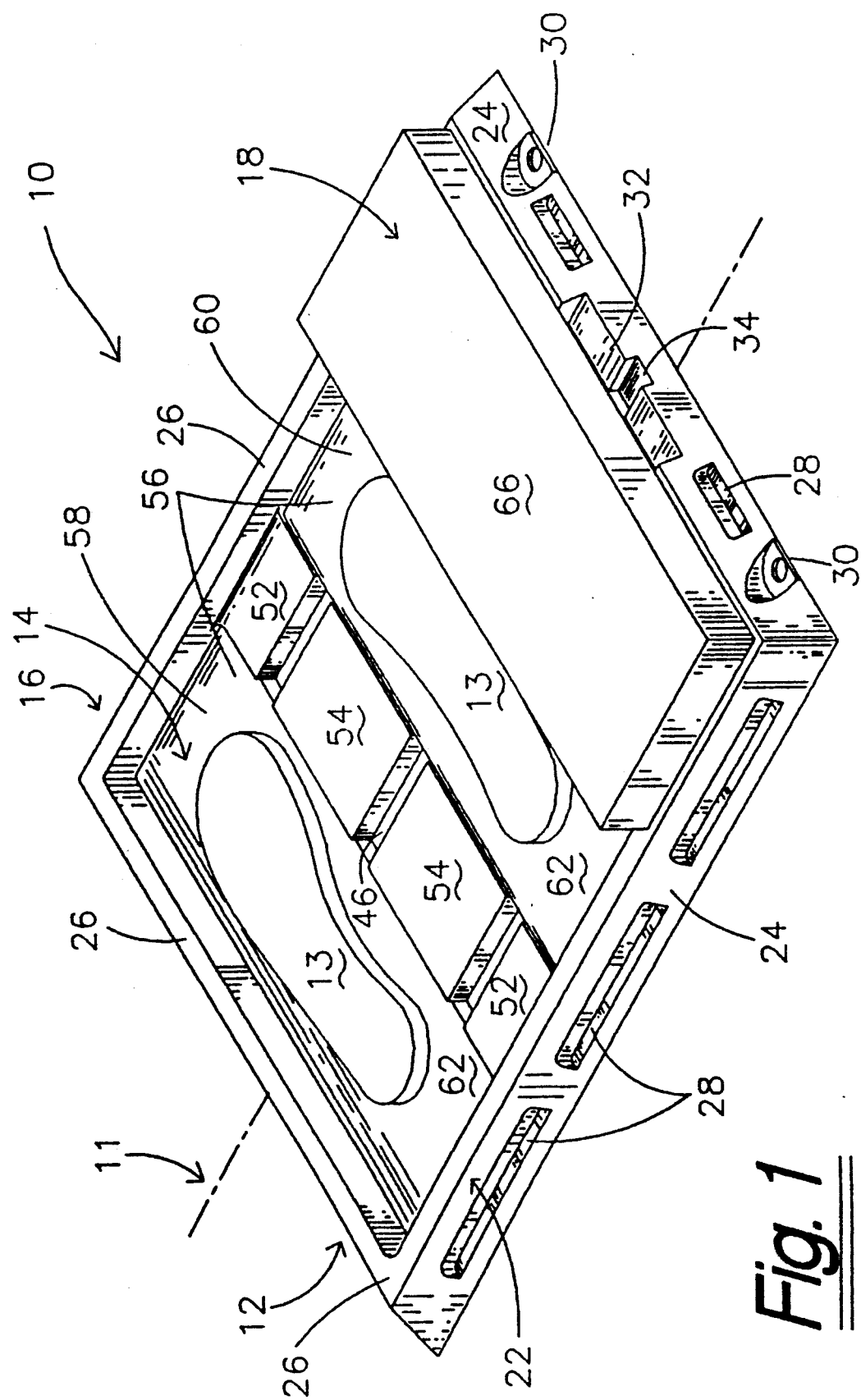
FIG. 1 is a perspective view of a self actuating sole wetting device according to the present invention.

Referring now to FIG. 1, the preferred embodiment of the self actuated sole wetting apparatus of the present invention is illustrated in a perspective view and designated by the general reference character 10. As may be seen in this illustration, the sole wetting device 10 is bilaterally symmetrical about a symmetry axis 11 and is primarily in the form of a tray assembly 12 which is adapted to receive the soles 13 of a person's feet or shoes or of an animal's paws within the sole receiving subassembly 14. The base tray assembly 12 is supported and held in position by a peripheral structure subassembly 16. A reservoir subassembly 18 provides wetting solution 20 to the receiving subassembly 14. In the illustration of FIG. 1 it may be seen that the soles 13 are situated within the sole receiving subassembly 14 for the purposes of wetting the bottom of the soles 13 with the wetting solution 20, thus effectively destroying any bacteria or viruses carried on the bottom of the soles 13.

Figure 2:
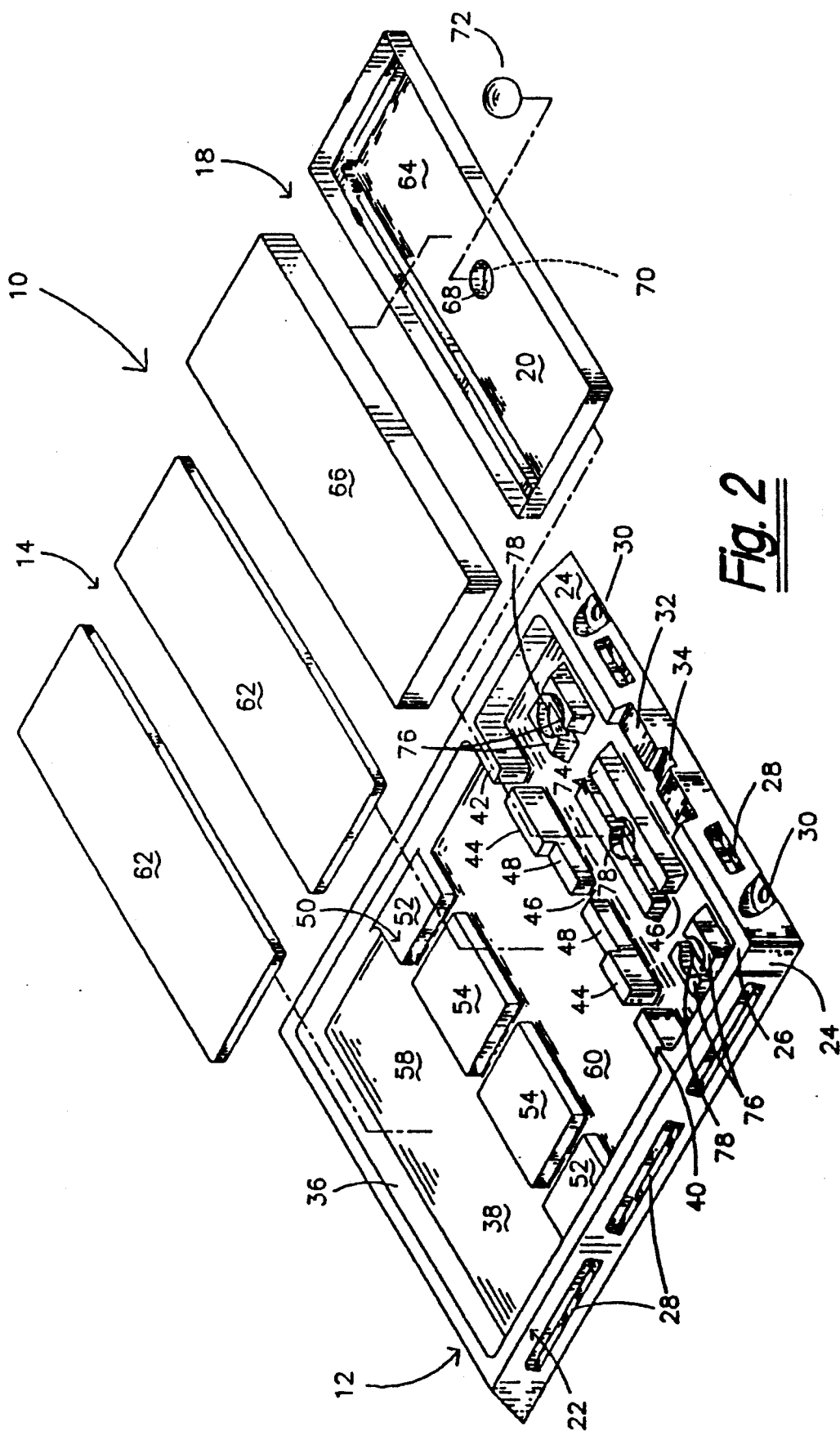
FIG. 2 is an exploded perspective view of the invention.

The precise structure of the various subassemblies is best understood from a consideration of FIGS. 1 and 2 taken together. The peripheral structure subassembly 16 is especially illustrated in FIGS. 1 and 2 while the reservoir subassembly 18 is illustrated primarily in FIG. 2.

The base tray assembly 12 is provided with structural integrity and positioning support by the peripheral structure subassembly 16. The peripheral subassembly 16 primarily includes a raised rim portion 22. The rim portion 22 includes, on each of the four sides of the base tray assembly 12, a flaring buttress member 24 which extends downward and outward from a rim panel 26. The flaring buttress portion 24 is flared outward from the rim panel 26 in order to provide good structural support and to prevent slippage. This also is considered an attractive appearance feature. Each of the flaring buttress portions 24 is provided with reinforcing ridges 28. The reinforcing ridges 28 are in the form of reinforced indentations into the surface of the flaring buttress 24 in order to utilize the plastic molding process to create reinforcement without utilizing an excess amount of material.

As is shown in both FIGS. 1 and 2, at least one side of the base tray assembly 12 is provided with securing detents 30 formed in the buttress 24. The securing detents 30 are utilized to permit the user to secure the sole wetting device 10 to a floor, wooden board or the like by use of screws or some other type of fastener. The securing detents 30 are useful in instances when it is desirable to make absolutely certain that the sole wetting device 10 does not slip or be moved inadvertently. Optionally, additional securing detents 30 may be formed on the opposite side of the base tray assembly 12, or even at additional locations if desired. The position shown in the drawing is largely a matter of design choice.

The rim panel 26 and the associated flaring buttress 24 on the side of the base tray assembly 12 adjacent to the reservoir subassembly 18 are provided with an exterior access detent 32 and an overflow channel 34. The exterior access detent 32 is provided to allow the user to obtain access to the adjacent portions of the reservoir subassembly 18 while the overflow channel 34 is provided to prevent the liquid level within the sole receiving subassembly 14 from becoming too high. If the liquid level is allowed to become too high then the benefits of the present invention are minimized. Therefore it is desirable to provide the overflow channel 34 to allow the liquid to escape to the exterior of the device, perhaps into a capture basin or a nearby drain, rather than to become trapped within the sole wetting device 10.

An interior wall 36 is provided about the interior of the base tray assembly 12 on the opposite edge of the rim panel 26 from the flaring buttresses 24. In the preferred embodiment 10 the interior wall 36 is essentially vertical and extends from the rim panel 26 to an interior floor panel 38. The exterior surfaces of the interior floor panel 38 are adapted to rest flat against the floor or support surface in order to support the weight of a human thereon.

Further structural integrity for the base tray 12 and support for the reservoir subassembly 18 is provided by a series of interior support ridges 40 which extend across the base tray subassembly 12 at the interior edge of the reservoir subassembly 18. The interior support ridges 40 include a pair of end ridge members 42 and a pair of central ridge members 44. Each of the interior support ridges 40 is separated from the next by a fluid flow channel 46. The end ridge members 42 are integrally formed with and extend from the rim panel 26, the interior wall 36 and the floor panel 38. The central ridge members 44 extend upward from the floor panel 38 and, at their exterior portions, are of a height equal to that of the end ridge members 42 and the rim panel 26. At the positions located nearest to the symmetry axis 11, the central ridge members 44 are provided with an interior access detent 48, serving the same purpose as the exterior access detent 32.

Additional interior structural support, as well as definition of the sole receiving subassembly 14, is provided by a series of divider blocks 50 extending across the base tray assembly 12. The divider blocks 50 are lower in height than are the interior support ridges 40 and extend only about half of the height of the interior wall 36. The divider blocks 50 include a pair of end blocks 52 extending out of the interior wall 36 and the floor panel 38 and a pair of central blocks 54 extending upward from the floor panel 38. Fluid flow channels 46 extend between the divider block members 50. The width of the block members 50 is sufficient to divide the sole receiving subassembly 14 into a pair of foot receiving chambers 56. These include a first foot chamber 58 and a second foot chamber 60, with the foot chambers 58 and 60 being separated by a distance which allows the average human user to stand comfortably with one foot in each of the foot chambers 58 and 60.

The foot chambers 56 provide the primary structure of the sole receiving subassembly 14. The first foot chamber 58 is defined by the interior wall 36 on three sides and by the divider blocks 50 on the fourth side while the second foot chamber 60 is defined by the interior wall 36 at its ends and by the divider blocks 50 and the interior support ridges 40 on its longitudinal sides. The height of each foot chamber 56 is defined by the height of the interior wall 36 and the divider blocks 50. The floor panel 38 provides the base for the chambers 56.

In the preferred embodiment 10, each of the foot receiving chambers 56 is provided with an absorbent pad member 62. The absorbent pad members 62 serve as wicking elements which draw up the wetting solution 20 and deliver it to the soles 13 when the person or animal stands in or walks through the foot receiving chambers 56. The absorbent pad members 62 are also compressible to allow the normal foot print of a person or animal to be compressed so as to achieve optimal distribution of the wetting solution 20.

The absorbent pad member 62 of the preferred embodiment 10 is selected to have a thickness of 1.3 cm 0.50 in) and to be compressible to a sixty to seventy-five percent degree. This has been found to be an appropriate construction to achieve an average depth of wetting solution 20 within the foot receiving chambers 56 of 0.63 cm (0.25 in). In this fashion, the fluid level is maintained below the uncompressed top of the absorbent pad member 62 but is above the level to which the pad member 62 compressed when stepped upon by a person or animal. Of course, the absorbent pad member 62, which is preferably constructed of open cell plastic scrubbing material, utilizes capillary wicking action to deliver the wetting solution 20 to the soles 13 even if a substantial compression is not obtained. However, compression increases the degree of wetting achieved.

The reservoir subassembly 18 provides the constant supply of wetting solution 20 to the sole receiving sole assembly 14. As is especially apparent from FIG. 2, the reservoir subassembly 18 includes a reservoir base 64 and a reservoir cover 66 which combines with the reservoir base 64 to provide a tank for containing the wetting solution 20. The reservoir base 64, includes, on the bottom surface thereof, a drain aperture 68 extending through a drain protrusion 70 which extends downward from the reservoir base 64. In the preferred embodiment 10 shown in the drawing an optional check valve 72 is provided within the drain protrusion 70 to regulate the flow of wetting solution 20 therethrough. The check valve 72 is not required in order to maintain the level but is desirable to limit the flow rate, especially in the instance of spills.

The reservoir base 64 is supported from below by a central support pedestal 74 formed on the floor panel 38 and a pair of end support pedestals 76. In the preferred embodiment 10 shown, each of the support pedestals 74 and 76 includes a circular centrally located drain receiving detent 78 and fluid flow passages 46 extending outwardly therefrom. The drain receiving detents 78 are provided on each of the support pedestals 74 and 76 in order to receive the drain protrusion 70 on the reservoir base 64. Although, in the preferred embodiment 10, the reservoir base 64 has a centrally located drain protrusion 70 such that it interfaces with and is supported by the central support pedestal 74, other embodiments of the reservoir subassembly 18 are envisioned which would have the drain protrusion 70 located at either end so as to mate with the drain receiving detent 78 of one of the end support pedestal 76. The additional pedestals may also support separate reservoirs filled with different liquids for special circumstances.

Each of the pedestals 74 and 76 has a flat upper surface to receive the bottom surface of the reservoir base 64 and to support the reservoir at a level approximately 2.5 cm (1.0 in) above the floor panel 38. Lateral support for the reservoir base 64 is provided by the interior wall 36 of a portion of the rim portion 22 and by the interior support ridges 40. In the preferred embodiment 10, the reservoir cover 66 is removable to allow placement of additional wetting solution 20 within the reservoir base 64. However, the seal formed between the cover 66 and the base 64 must be airtight, since hydraulic leveling is used as the dispensation control method. Access to the reservoir cover 66 is achieved through the exterior access detent 32 and the interior access detent 48. It is also envisioned that an alternate reservoir 18 may be utilized which is integrally formed and is filled through the drain protrusion 70.

In the preferred embodiment 10 the base tray element 12 is a unitary molded component formed out of any of a variety of plastic sheet materials. The molding is formed in such a manner that the wall thickness at essentially all points is approximately 2.3 cm (0.90 in). Accordingly, the base tray element 12 includes open spaces on the underside of the rim portion 22, the interior support ridges 40, the divider blocks 50 and the support pedestals 74 and 76. These help to reduce the cost of manufacture, as does the bilateral symmetry.

Although the preferred material for the absorbent pad member 62 is open cell plastic scrubbing material, other materials such as sponge and compressible screening have also been found to be acceptable. It is desirable that the absorbent pad members 62 be easily replaceable in order to facilitate inexpensive upkeep without the necessity of moving the base tray assembly 12. With a selection of the scouring pad material, the absorbent pad member 62 also serves the purpose of being a method for cleaning the shoes and feet, which may be an advantage when placed near an exit door an or entrance door to a building. If the self actuating sole wetting device 10 is utilized as a shoe cleaning device as well, it may be necessary to replace the absorbent pad member 62 on a more frequent basis.

Although the present invention has been described above in terms of the best presently known embodiment and in terms of specific materials and dimensions, it is understood that a wide variety of alternatives are available. Many changes in materials and dimensions may be made without altering the invention. For example, different dimensions for the sizes of the foot receiving chambers 56 may be selected, and alternative methods of providing constant level liquid within absorbent pads 62 may also be utilized.

Various other modifications and alterations of the components and assemblies may be made without departing from the invention. Those skilled in the art will readily recognize additional embodiments and uses. Accordingly, the above disclosure is not to be considered as limiting and the appended claims are to be interpreted as accomplishing the entire spirit and scope of the invention.

INDUSTRIAL APPLICABILITY

The self actuated sole wetting device 10 according to the preferred embodiment of the present invention is straightforward and simple in its usage. It is adapted for easy usage by ordinary persons without special preparation or skills.

It is expected that the device 10 will be disassembled when first delivered and the user will need to place the absorbent pad members 62 within the foot receiving chambers 56. In addition, the user will secure the reservoir base 64 in position on the support pedestals 74 and 76, with the drain protrusion 70 extending into the corresponding drain receiving detent 78. The user will then fill the reservoir base 64 with a wetting solution 20 selected to achieve the particular purpose desired and then secure the reservoir cover 66 on the reservoir base 64. For the hydraulic siphon balancing technique of the present invention to operate properly, the seal between the cover 66 and the base 64 must be airtight. If an alternate, integral reservoir 18 is utilized, the reservoir will be filled first and then placed on the pedestals.

Once the wetting solution 20 has been placed within the reservoir base 64 the wetting solution 20 will began to be distributed along the floor panel 38 by the fluid flow channels 46 into the foot receiving chambers 56. The optional check valve 72 will limit the rate of flow of the liquid into the drain receiving detent 78, although hydraulic pressure will serve the same purpose once the fluid level in the base tray member 12 achieves the same height as the bottom of the drain protrusion 70. The check valve 72 also acts to prevent excess spillage in the event of a leaking reservoir or seal. The dispersal of the wetting solution 20 through the base tray member 12 is achieved through the fluid flow channels 46. The height of the fluid level may be adjusted by altering the height of the drain protrusion 70, for example by propping the reservoir base 64 at a height slightly higher than the top of the support pedestals 74 and 76.

Once the appropriate level of the wetting solution 20 has been achieved within the foot receiving chambers 56 the device 10 is ready for use. The user merely steps with one foot in each of the first foot chamber 58 and the second foot chamber 60 for a short period of time to allow the wetting solution 20 to coat the bottoms of the soles 13. This may also be accomplished simply by walking through the device 10. In the case of animals, they may be encouraged to step into the foot receiving chambers 56 in such a manner that the bottom of the paws may receive some of the wetting solution 20.

Each usage of the sole wetting device 10 is dependent primarily upon the nature of the malady involved. In the case of Parvo, the primary utilization is expected to be a placement of the device 10 at entrances and exits to kennels and other animal habitat areas. Other usages, such as placing the device near showers, are also envisioned.

All of the above described aspects and advantages of the present invention make the invention desirable for usage in personal and commercial circumstances. Accordingly, it is expected that the present invention will enjoy immediate, long lasting and widespread industrial applicability and commercial utility.

We claim:

1. A device for wetting the soles of the feet with a selected fluid, comprising:
    an enclosing tray, said enclosing tray being sufficient in extent to receive a foot horizontally therein, and capable of holding the selected fluid therein;
    fluid dispensation means for maintaining a relatively constant level of the selected fluid within said enclosing tray, said fluid dispensation means including a sealed reservoir having a single, downward depending protrusion, said single downward depending protrusion having an opening extending into said enclosing tray such that the opening of said single downward depending protrusion lies beneath said level of the selected fluid such that hydraulic leveling maintains said level of the selected fluid; and
    a compressible stepping surface within said enclosing tray such that the upper extent of said compressible stepping surface is above said constant level when uncompressed but beneath said level when compressed.

2. The device of claim 16 wherein
    a check valve is further provided within said single downward depending protrusion, in order to limit fluid flow therethrough.

3. The device of claim 1 wherein
    said constant level of fluid is maintained below a maximum level by providing an overflow channel in said enclosing tray.

4. The device of claim 1 wherein the compressible stepping surface is in the form of a liquid wicking material capable of maintaining a degree of wetness on the upper surface thereof, even though said upper surface is situated above said constant level of fluid.

5. An apparatus for delivering selected liquid to the soles of feet, shoes, and paws comprising:
a tray member having at least one foot receiving chamber formed therein, each said foot receiving chamber being formed so as to contain a desired level of a selected liquid therein;
removable pad members capable of fitting within said foot receiving chamber in such a manner that stepping on the removable pad members results in transfer of a quantity of the selected liquid to the soles; and
liquid dispensation means for maintaining said desired level of the selected liquid by hydraulic pressure, said liquid dispensation means including a reservoir having a hollow protrusion, including an opening therein, depending downward into said tray member, the opening of the hollow protrusion laying beneath said desired level of the selected liquid.

6. The apparatus of claim 5, wherein
said removable pad members are compressible such that the upper surfaces thereof extend above said desired level when uncompressed but lie below said desired level when compressed.

7. The apparatus of claim 5, wherein
said removable pad members are open cell plastic scouring pads.

8. The apparatus of claim 5, wherein
the tray member is bilaterally symmetrical about at least one symmetry axis.

9. The apparatus of claim 5, wherein said tray member includes
a peripheral structural subassembly providing side walls, dividing ridges and floor panels for said foot receiving chambers, and further providing support means for said liquid dispensation means.

10. The apparatus of claim 9, wherein
said peripheral structural subassembly includes a rim portion having a set of horizontal rim panels and a circumferential set of flaring buttress members extending outward and downward from said set horizontal rim panels, with open space existing beneath said rim panels.

11. The apparatus of claim 5, wherein said tray member includes
a plurality of mounting detents formed thereon for securing said tray member to a mounting surface.

12. The apparatus of claim 5, wherein
said tray member is an integrally molded component having effectively uniform wall thicknesses throughout.

* * * * *